United States Patent [19]
Gittleman

[11] Patent Number: 5,803,735
[45] Date of Patent: *Sep. 8, 1998

[54] FOOD INGRESS SHIELD FOR DENTAL PROSTHODONTIC APPARATUS

[76] Inventor: Neal Gittleman, 15 Greenway Plz. #1D, Houston, Tex. 77046

[*] Notice: The term of this patent shall not extend beyond the expiration date of Pat. No. 5,564,928.

[21] Appl. No.: 730,092

[22] Filed: Oct. 15, 1996

Related U.S. Application Data

[63] Continuation-in-part of Ser. No. 374,933, Jan. 18, 1995, Pat. No. 5,564,928.

[51] Int. Cl.$^6$ ............... A61C 13/225; A61C 13/263
[52] U.S. Cl. ............................ 433/180; 433/172
[58] Field of Search ................ 433/180, 169, 433/172, 173, 174, 181

[56] References Cited

U.S. PATENT DOCUMENTS

| | | | |
|---|---|---|---|
| 3,827,145 | 8/1974 | Richards | 433/175 |
| 4,318,696 | 3/1982 | Kasama et al. | 433/169 X |
| 4,738,622 | 4/1988 | Kawahara et al. | 433/169 |
| 5,006,068 | 4/1991 | Lee et al. | 433/169 |
| 5,064,373 | 11/1991 | Staubli et al. | 433/173 |
| 5,106,299 | 4/1992 | Ghalili | 433/172 |
| 5,125,839 | 6/1992 | Ingber et al. | 433/173 X |
| 5,275,560 | 1/1994 | Obersat | 433/172 X |

*Primary Examiner*—John J. Wilson
*Assistant Examiner*—Yvonne R. Abbott
*Attorney, Agent, or Firm*—Ezra L. Schacht

[57] ABSTRACT

A method and apparatus for setting and removing a cemented, retrievable prosthodontic appliance by means of a levering instrument applied to the gap between two parallel surfaces, the first surface being a flat-topped ledge of a window on the lingual aspect of a dental prosthesis and the second surface being at least one opposed step or ledge on an artificial implant abutment. This invention combines the evenly stressed strength of a permanently cemented prosthesis with a damage free method of prosthesis removal without undue forces on the underlying implant. A conformal, removable plug of durable polymer fills and is securable within yet removable from the window in the completed restoration.

4 Claims, 10 Drawing Sheets

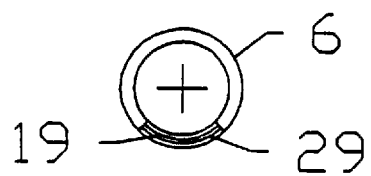
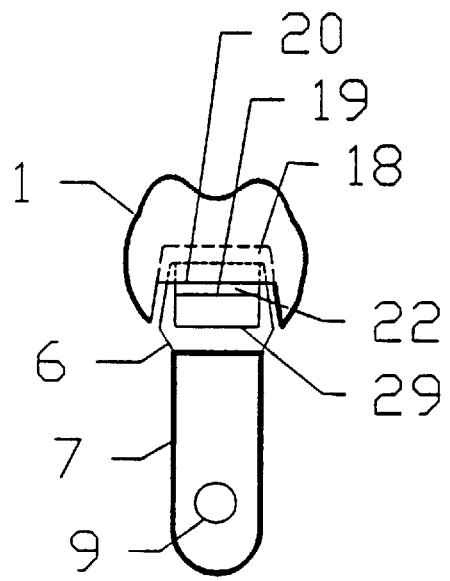
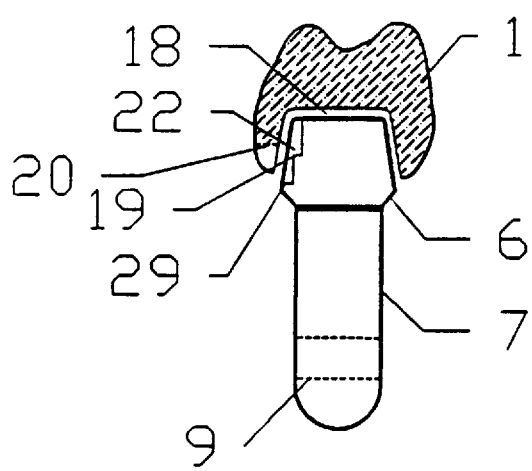
Fig. 2c
Fig. 2a
Fig. 2b

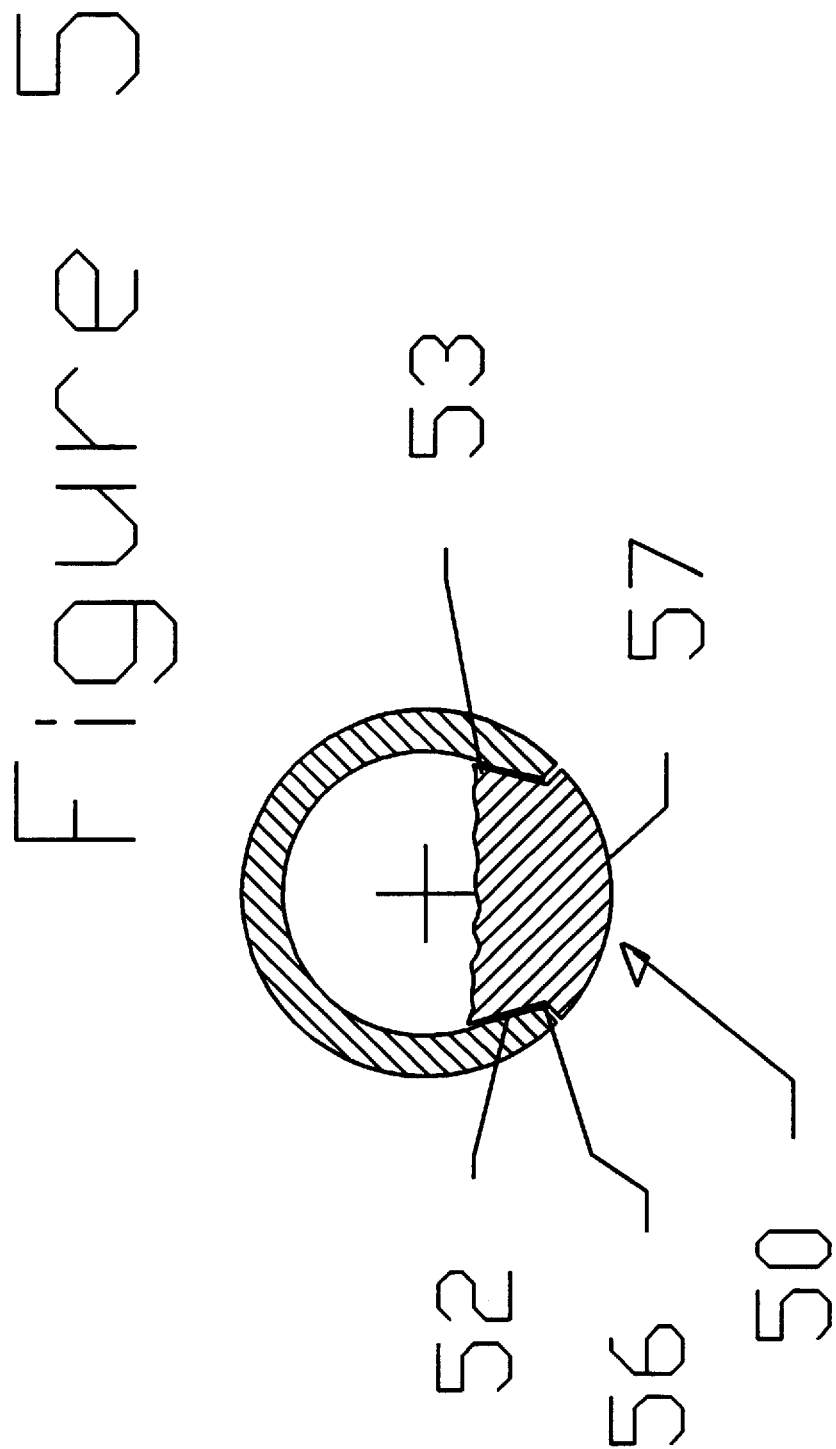

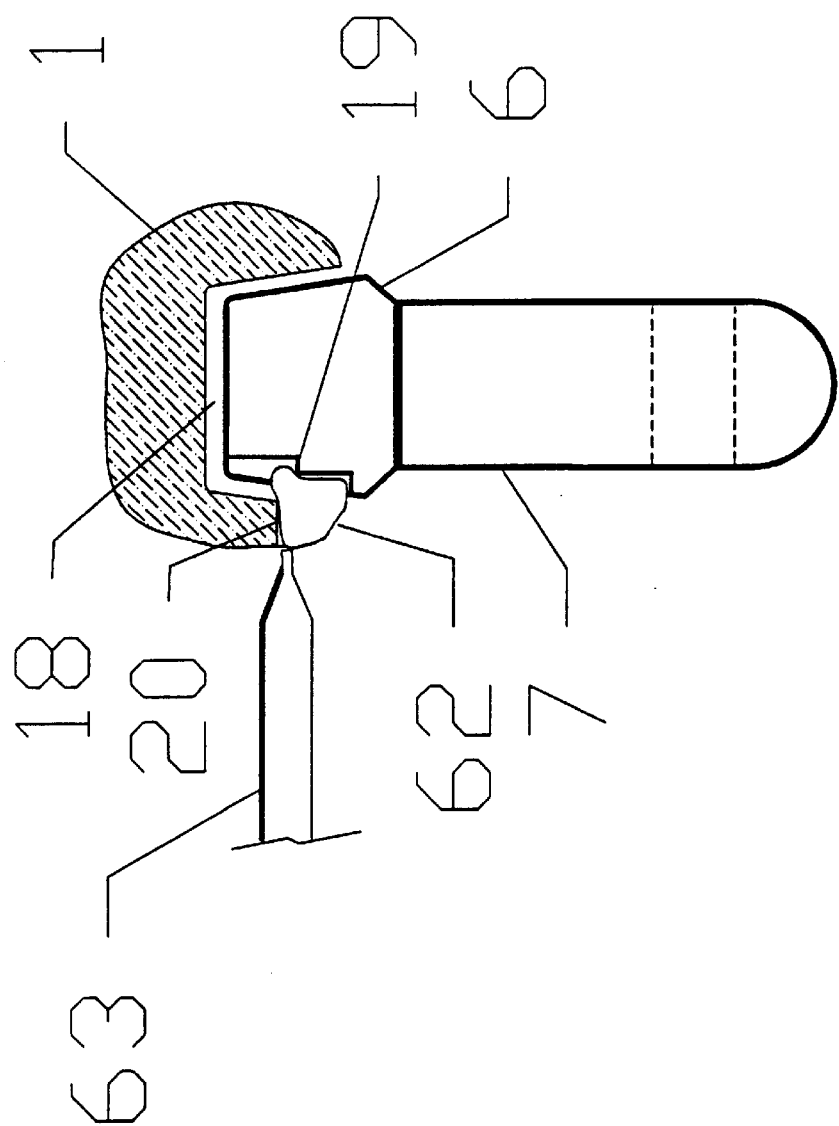

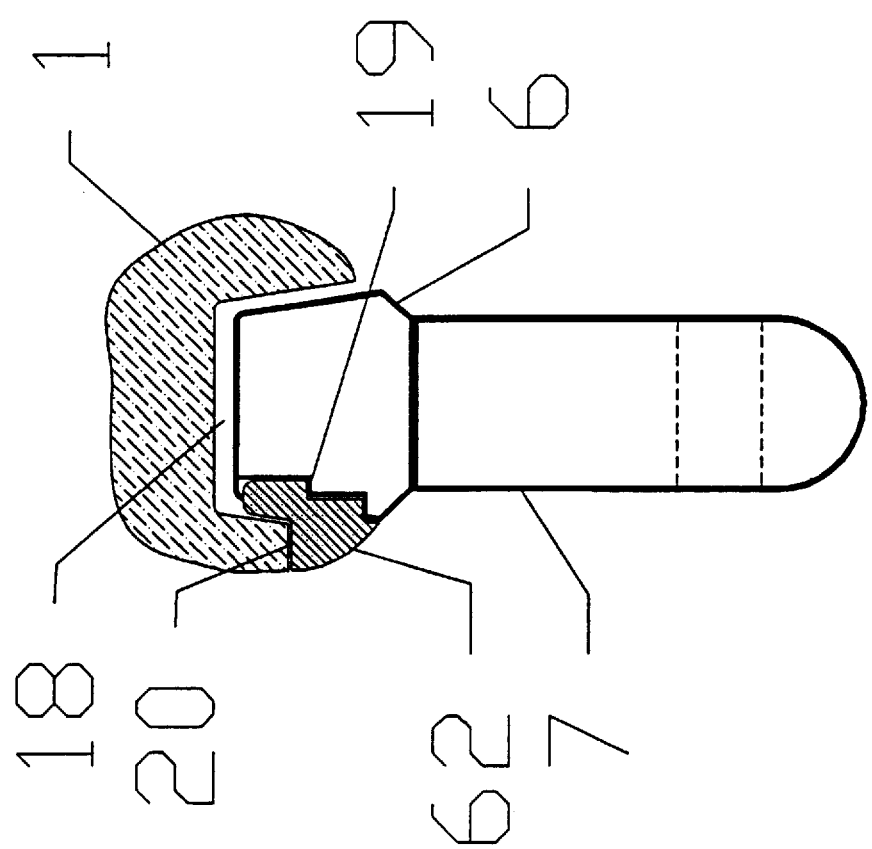

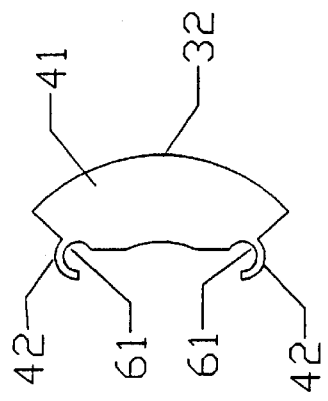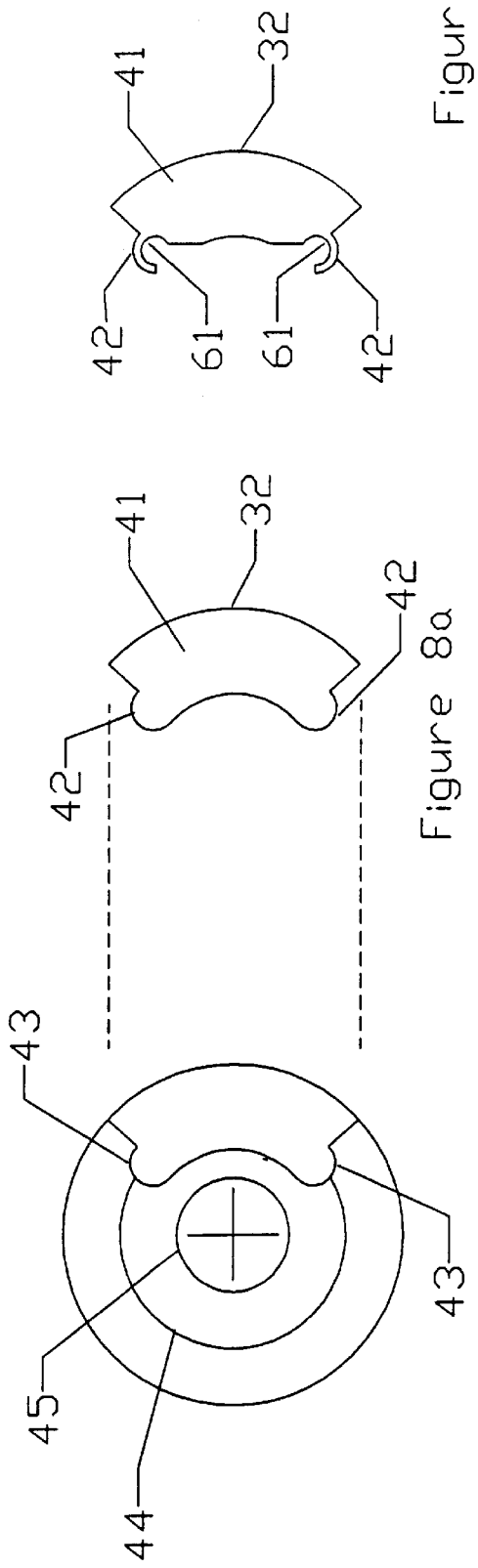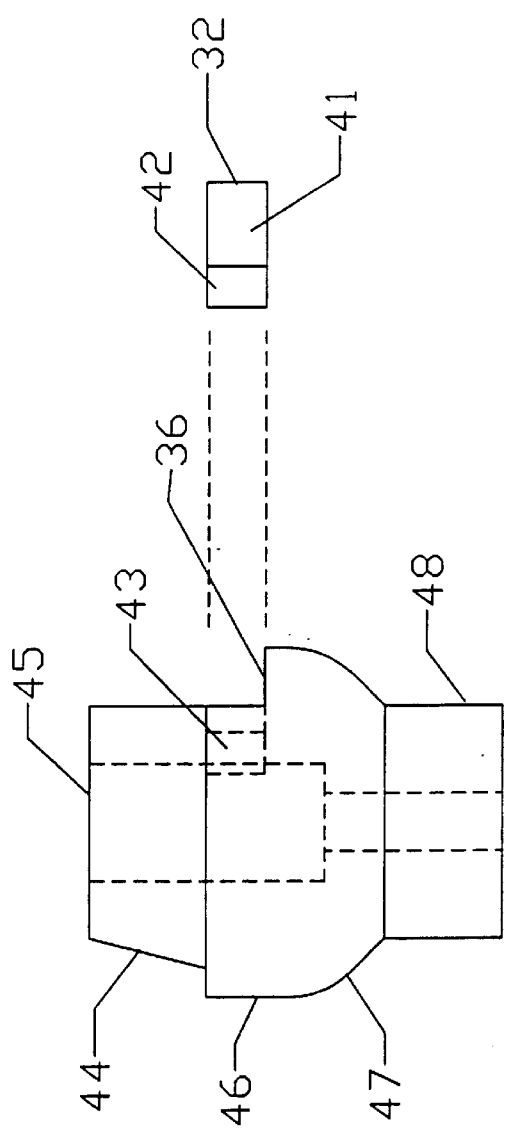

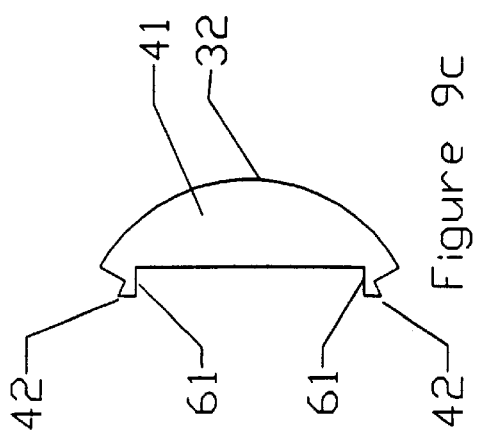
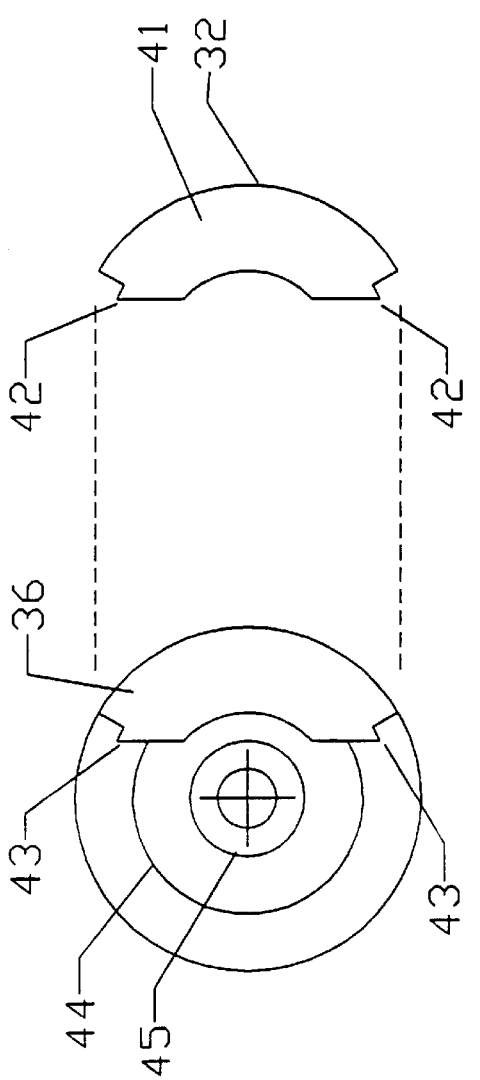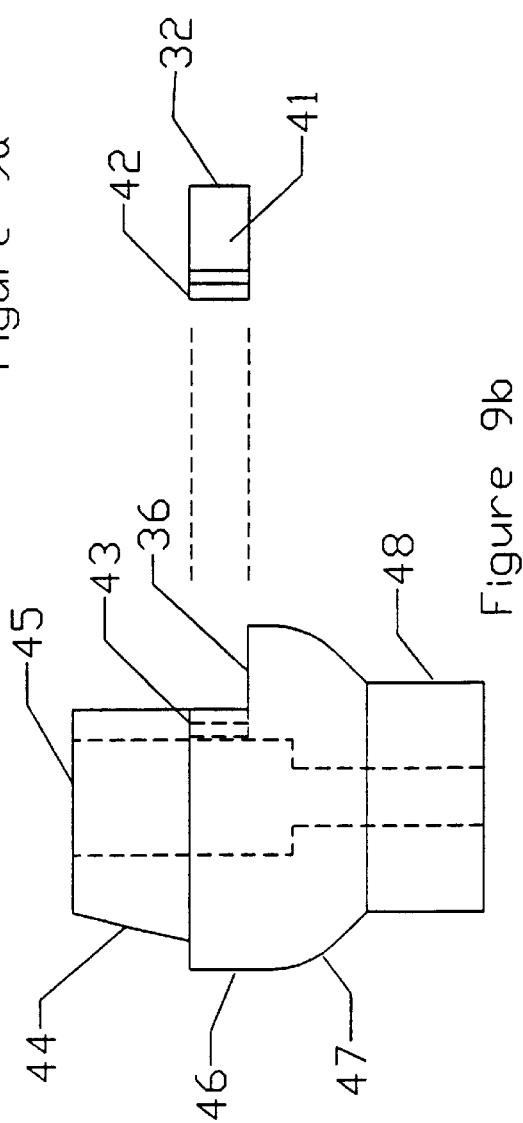

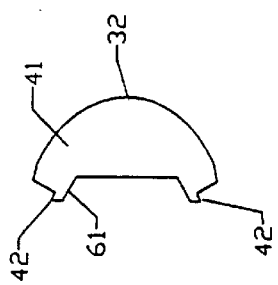
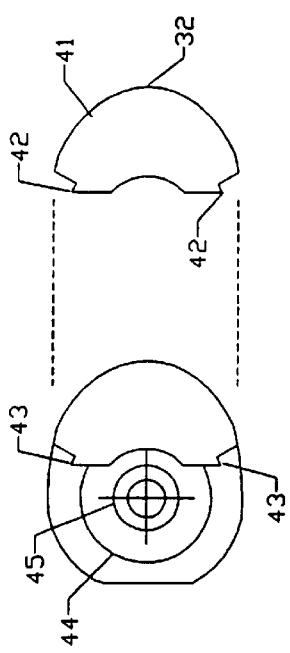
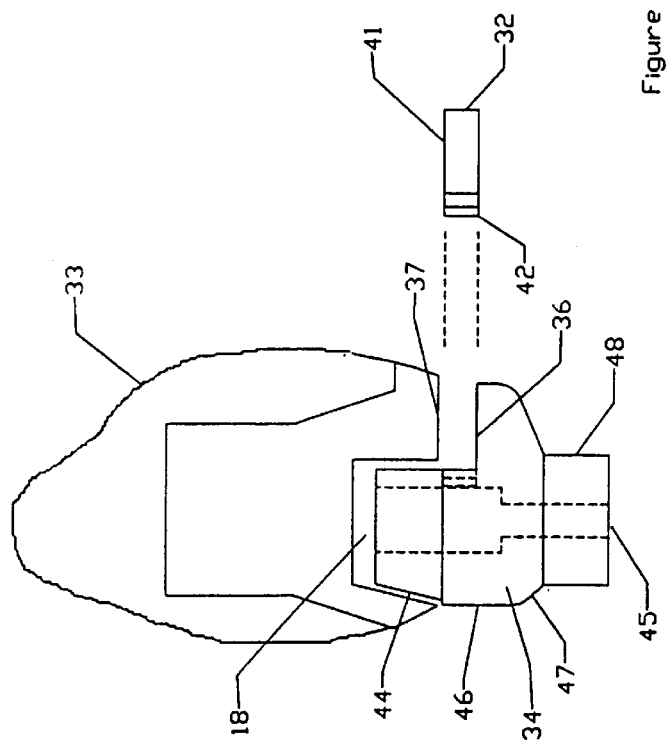

5,803,735

FOOD INGRESS SHIELD FOR DENTAL PROSTHODONTIC APPARATUS

CROSS REFERENCES TO OTHER APPLICATIONS

This application is a C.I.P. of U.S. application Ser. No. 08/374,933, filed Jan. 18, 1995, now issued as U.S. Pat. No. 5,564,928 and made of reference in this application.

BACKGROUND OF THE INVENTION

Present dental practices tend toward the replacement of lost teeth with cylindrical or plate metal alloy implants embedded in the bone of the mandible or maxilla to support the artificial tooth restoration. If extensive replacement of several teeth is needed, several implants, alone or in conjunction with existing teeth prepared as abutments, are used to anchor the replacement prosthetic teeth. As the number and complexity of support abutments are increased, the difficulty in aligning and fastening the prosthetic restoration increases. The use of several mechanically connected parts at each post or plate implant site, adds to the possibility of misalignment or biomechanical failure. This invention describes a method and apparatus to provide a simpler mechanism and more direct technique for securing a permanently cemented, yet retrievable prosthodontic appliance while still offering a durable mechanical support.

The last two decades have led to a revolution in implant prosthodontics. Titanium alloy implant cylinders or plates are intimately installed in holes or slots drilled in the underlying bone. It is the practice to allow several months to pass while the underlying bone bonds to the surface of the implant. Por this reason, implants are provided with at least one threaded hole on the crestal surface or edge. These holes are temporarily capped with a healing screw to prevent the downgrowth of soft tissue and bone into the internal threads. The soft tissue is sutured over the implant until the intimate metal-bone bond is effected.

At the next surgical encounter, the soft tissue is resected and the healing screw is replaced with a metal alloy perimucosal extension of selectable height and emergence profile and the soft tissue is sutured around the base of this extension. This extension is usually bolted in place and prevented from rotating by means of locating pins and holes or internal and external matching hexagonal (or other regular polygon shaped) projections. These perimucosal extensions form the support for artificial abutments used to support the final prosthetic restoration. The final prosthodontic restoration requires a close mechanical mating between the abutments and the matching internal aspect or underside of the prosthesis. These closely matched parts often consist of telescoped, tapered cylindrical surfaces requiring a tight, non-binding, "passive" fit. This places inordinate requirements on the precision and technical skills of the dentist and the laboratory technician. Parallel alignment of the axes of each abutment to prevent binding of tapered fits cannot be easily guaranteed. The present invention, relying on a conformable, cemented boundary, circumvents these objections.

Much of the current discussion in the field of dental implantology centers around the durability and maintainability of the various methods of attaching the final restoration to the underlying abutments. Bolting with threaded fasteners through the occlusal surface of the restoration and back filling with composite materials complicate the cosmetics and the retrievability of the prosthesis. Bolting through the non cosmetic, lingual side of the prosthesis has the additional requirement for a greater thickness or metal to provide mechanical support, thus reducing room for the tongue and potentially affecting speech, and the periodontal health of the abutment. Excessive inline or rocking pressure transmitted to an individual implant from the overlying restoration may lead to frank implant failure Failures may occur from the loosening of a screw caused by thread walking or the backing out of a screw by micro-movements. The shifting of an abutment from repetitive stresses exceeding the elastic limits between the screw thread and the internal thread of the implanted post or plate may cause the flexure or excessive loading of a single implant. Long term changes in the underlying bone structure in response to uneven stresses may lead to the loss of an individual dental implant. For each additional mechanically attached connection, alignment errors accumulate and reduce the likelihood of a good nonbinding, stress free "passive" fit.

The present invention acts to equitably distribute the loading forces with a retrievable dental cement between the matching faces of the abutments and the internal aspect of the final restoration. Each abutment is made with at least one step or shelf on the lingual face to act as a bearing surface for a removal instrument. The final prosthesis is equipped with a flat-topped window ledge on the lingual side. There is a matchingshelf on the implant abutment, with enough space between the surface of the shelf and the flat top of the window for the introduction of a wedge-tipped extraction instrument. This instrument is used to apply a prying force between each abutment and the mating ledge in the underside of the final restoration. The prying instrument applies an even opposing force between the overstructure and the abutment eliminating the potential damage to both structures. Prior methods of removing cemented restorations involved hammering movements under much less control. The method and apparatus of this invention in combination with an appropriate dental cement, yields a predictable technique for securing, yet retrieving the final restoration.

[REMAINING PROBLEMS ARE THE SUBJECT OF THIS CIP APPLICATION Although the apparatus and method disclosed in parent application Ser. No. 08/374,933 are effective as a retrievable cemented prosthodontic device, a problem remains with the ingress through window 22 and the accumulation of food particles within the [spaces] window 22 (FIGS. 2 a, b).]

PREFERRED EMBODIMENT OF THE FOOD INGRESS PREVENTION SHIELD

A conformal removable and replaceable plug of resilient, durable polymer, such as a high durometer rubber, flexible silicone rubber compound or urethane may be secured within the window to provide a continuous smooth lingual aspect to the cemented restoration and the adjacent prothesis. In addition to the smooth non-irritating surface presented to the tongue, the plug may be made with such precision that a liquid- and gas-tight seal between the plug and the mating surfaces is achieved. In this way, a second objective of preventing the ingress of food particles, which can lead to bacterial fermentation and noxious odors is accomplished. Another objective is the use of a prying tool, similar or identical to tool 21 of FIG. 3, since the resilient rubbery nature of the plug allows for forced removal. In combination with grooves, retaining recesses, or a shallow reverse draft in the window, the plug may also be securely held in place.

The plug can also be slightly oversized to offer a compression seal against the window surfaces. The plug can be "hard surfaced" on the lingual aspect with a polymer of higher durometer by chemical, thermal or other means known to those skilled in the art. Alternately, a thin, hard metal or porcelain cover bonded to the resilient plug may provide a lingual surface with a longer useful service life.

And, of course, the plug lends itself to production with standard plug and window dimensions to aid the dentist in fitting the prosthesis. Nor should caulking with photo-curable silicone or other polymers be ignored as an eminently practicable method of casting this plug in place. This thixotropic bonding material, extruded into the window, is hardened in place with a short exposure to the UV or blue curing light. Another embodiment of the invention places the window in the abutment near or at the soft tissue margin. The upper ledge of the window is supplied by the flat surface on the bottom lingual side of the prosthesis, while the lower ledge of the window is formed by an inset undercut shelf in the abutment. A prying tool can be introduced to carefully separate the retrievably cemented prosthesis from the abutment. A molded plug made from a biocompatible and durable plastic compound can be dropped into place within the abutment inset undercut just prior to bonding the prosthesis into place. Projections on the drop-in molded plug match recesses in the abutment inset undercut and act to prevent the plug from slipping out. The projections and matching recesses are of sufficient size and shape to retain the molded plug, yet allow for removal by the proper application of force with a dental pick. The purpose of the molded plug is to prevent the ingress of food particles and to facilitate good oral hygiene.

BRIEF DESCRIPTION OF THE DRAWINGS

FIG. 2a and 2b display a cross sectional front and side view of a single implant with abutment "steps" and secondary restoration with "window";

FIG. 2c is a top view of the abutment;

FIG. 4 b, added in this C.I.P., is a cross sectional exploded view of a single implant conformal plug 30;

FIG. 5, [added in this C.I.P.,] is a cross sectional view of a plug designed to mate more securely with a prothesis, the assembly comprising an improved apparatus design and some simplified methods for their use by the dental practitioner;

FIG. 6, details an elevated view of a polymer compound injector mechanism for filling in the window between an abutment and the prosthesis;

FIG. 7 shows an elevated view of the cured polymer plug;

FIG. 8a details a plan and figure 8b details an elevated view of a self-retaining, molded drop-in window plug for window located in the lingual aspect of a cementable, screw retained abutment;

FIG. 8c shows an alternate molded plug profile with snap-in projections;

FIG. 9a details a plan and FIG. 9b an elevated view of an alternate self-retaining, molded drop-in window plug located in the lingual aspect of a cementable, screw retained abutment;

FIG. 9c shows an alternate molded plug profile with snap-in projections;

FIG. 10a shows a plan and figure 10b an elevated exploded views of a self-retaining, molded drop-in window plug and corresponding abutment with an scalloped emergence profile and window with a cross section of a prosthesis shown in place over the abutment; and FIG. 10c details a plan view of a molded plug with snap-in projections.

DETAILED DESCRIPTION OF THE DRAWINGS

Figure 1:
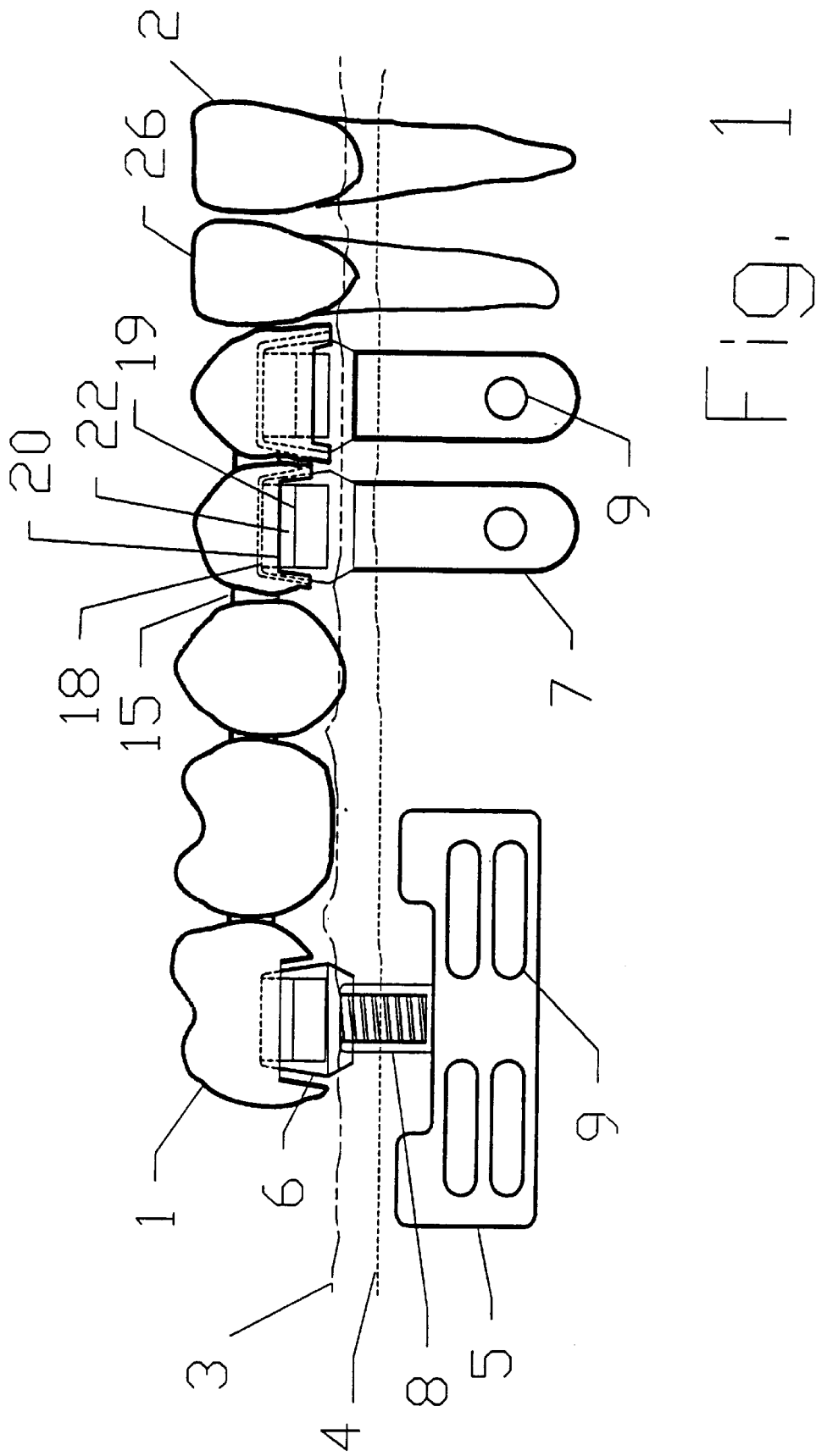
FIG. 1 shows a cross sectional elevated view of a final restoration with various means of support.

The partially edentulous lower left jaw, shown schematically in elevated view from the lingual side in FIG. 1, illustrates the combination of methods used to secure the secondary prosthesis 1. Natural tooth 2 is not modified, nor is its nearest neighbor 26.

The next five dental positions are replaced with the prosthesis 1, with each artificial tooth bridged by the underlying structural member 15. The bone surface 4 is shown with it's overlying soft tissue margin 3. Typical plate implant 5 and post implant 7 are firmly set within the bone 4 with extension penetrating through the soft tissue 3. The plate extension 8 has an internal thread and coupling means to retain tapered and stepped abutment 6. Post implant 7 rises through the soft tissue margin 3 and terminates in a similar tapered and stepped abutment. This abutment has a step or shelf 19 shown extending for a distance circumferentially around the long axis of the post implant and opposing the parallel, flat-topped ledge 20 of a lingual side window 22 in the prosthetic appliance The gap or window 22 between these two parallel surfaces allows for the introduction of a prying or twisting tool to part the overlying prosthesis from the abutment underneath.

Cement applied within the bonding space 18 between the prosthesis and the abutment acts to firmly retain the prosthesis to the abutments with an even distribution of forces. This prevents any undue stresses on any one abutment.

FIG. 2a presents an elevated view of a typical single post implant 7 with a perforation 9 to allow for ingress of bone growth for additional reinforcement. Prosthesis 1 may be removed by application of opposing force between surface 20 of the prosthesis and surface 19 of the post abutment 6, together forming the toy and bottom of window 22. Since the forces are in opposition, minimal pulling or twisting forces are transmitted to implant post 7 with less chance of loosening the implant or breaking the prosthesis. Multiple shelves 19 and 29 accommodate different elevations for the proper design of and access to the window 22 of the prosthesis. FIG. 2c shows the plan view of the top of the abutment post with the shelves or steps 19 and 29 extending for some distance around the circumference of the post abutment 6.

Figure 3:
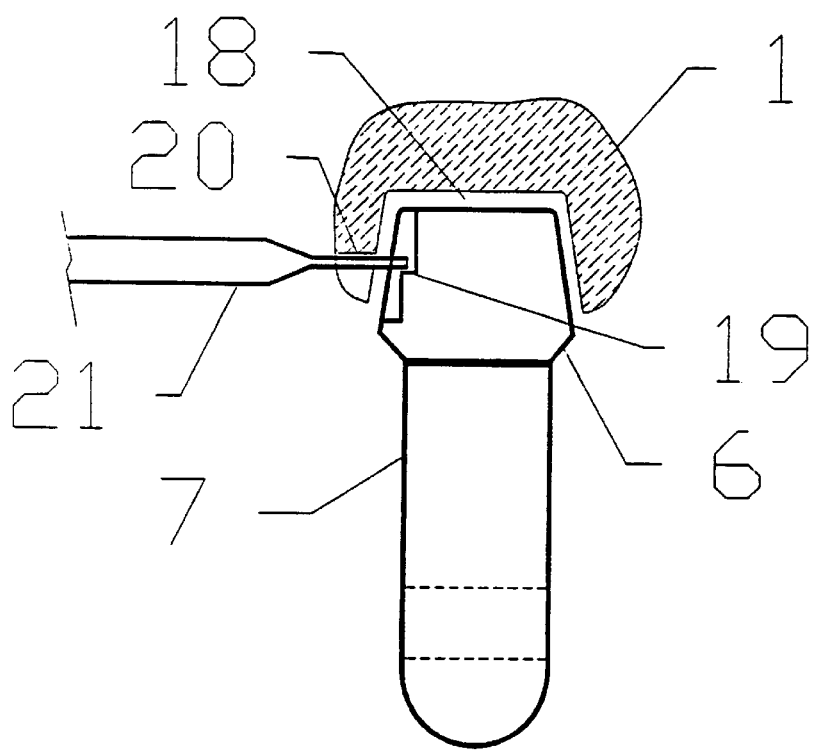
FIG. 3 details a cross sectional view of the prying instrument in use.
Figure 4A:
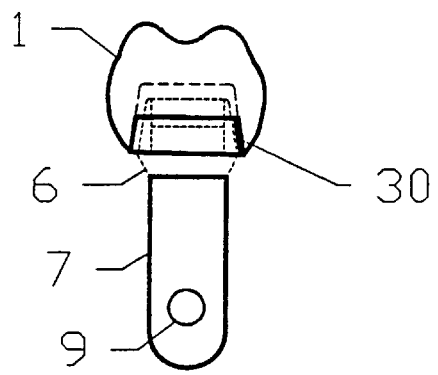
FIG. 4 a, added in this C.I.P., is a front view with abutment "steps" and conformal plug 30.
Figure 4B:
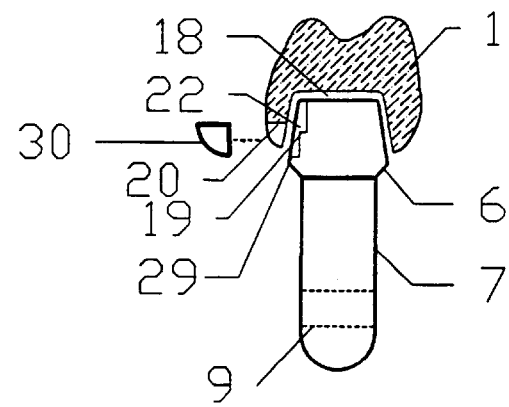

FIG. 2b shows the elevated sectional view through the post implant 7. Shelf 19 and opposing flat-topped window ledge 20 show the area of force application. FIG. 3 illustrates the use of a tool 21 to pry between shelf 19 and ledge 20 to part the cement in the bonding space 18 by the application of levered force. The proper choice of cement joining the surface of abutment 6 and the internal aspect of prosthesis 1 determines the maximum force needed for removal.

FIG. 3 gives an elevated sectional view of one member of the prosthesis 1 and a post implant 7 with its attached abutment 6.

The step or shelf 19 of the abutment 6 and the opposing flat-topped ledge 20 of the window 22 in prosthesis 1 form the gapped parallel mating surfaces against which the prying instrument is worked. The flat blade of the prying instrument applies force to the opposing surfaces 19 and 20 and shears the cement bond in the bonding space 18 to release the fixed retrievable prosthesis 1.

The provision of a chamfer 52 in FIG. 5. rather than the radial sides 51 of the aperture in FIG. 2c enables two additional embodiments of value, one in apparatus and one in method of use.

In FIG. 2c, a plug 50 can too easily come out of the aperture during mastication and tooth brushing. In FIG. 5, the angle of chamfer 52 makes it much more difficult to remove the plug 50. It should be noted that the inner diameter 53 of plug 50 is much larger than the inner diameter 56 at the outer edge of the chamfer 52, providing a "keystone like" effect to secure the plug 50 until removed by the dental practitioner.

As to methods, in FIG. 6. in a first method a small mass 62 of silicone or other polymer can be placed in the cavity, and with his finger tip or spatula, the practitioner can round the exterior surface of the moldable material to blend with the adjacent prothesis surface.

Alternately, in FIG. 5, a plug 50 can be molded to dimensions that will duplicate those of the window aperture, except that the plug can be slightly larger The plug can then be pressed into the aperture, where the larger end 53, expanding into the aperture, will secure it in the same keystone fashion.

In FIG. 6, a syringe 63 filled with a paste-like, curable compound, is used to express some of the compound 62 into the window between the abutment 6 and the prosthesis 1 This compound can be any of a number of biocompatible formulations known to the skilled dental practitioner. The compound can be smoothed with a spatula or the finger to form a smooth continuum on the lingual aspect of the restoration prior to curing into a hardened mass. In FIG. 7, the compound 62 completely fills the window void 22 in a hardened state.

FIG. 10a and 10b, in exploded views show the molded drop-in window plug 41 with interlocking projections 42 and recesses 43 providing an effective retention of the plug when overlay prosthesis 33 is cemented in place. This molded plug 41 is captive between flat surface 37 on the bottom lingual margin of the overlay prosthesis 33 and the parallel opposed, flat surface 36 of the abutment 34 forming a window 22. The molded window plug projections 42 are designed to "snap" in or out of the recesses 43 between flat surfaces 36 and 37 and will provide a seal against debris. Outer curved surface 32 of the molded plug provides a tight, continuous seal with the emergence profile of the abutment 34 and overlay 33. The emergence profile, on the lingual aspect, offers a wider shelf for improved purchase of the prying tool.

FIG. 10c details a thinned section 61 of the molded plug 41 designed to allow projections 42 to flex into the mating recesses 43 on the abutment 34. Similar thinned sections 61 can be molded into the plug 41 detailed in FIG. 8c to allow the plug to be snapped in and out of the prying window 22.

In FIG. 10b, the collar 46 of the abutment 34 extends through the margin of the gum with an emergence profile 47 that closely mimics that of the natural tooth. The cylindrical projection 48 makes an intimate, non-rotating mechanical connection to the underlying post implant (not shown) by means of a threaded fastener (not shown) through interior hole 45. The tapered projection 44 of the abutment is retrievably cemented to the overlay restoration 33

The overlay restoration 33 is shown as a cosmetic porcelain over metal but is not limited to this composite. The window 22 formed by flat surfaces 37 and 36, when freed of molded plug 41, provides a space for insertion of and action by a suitable prying tool to free the overlay prosthesis without damage.

FIG. 8a and 8b show another embodiment of the locking mechanism for the molded drop-in plug 41. The plug can be made from a biologically acceptable plastic compound, such as one of the polymethacrylates. Projections 42 and recesses 43 can be sized to be dropped into place just prior to cementing the prosthesis in place and yet allow for removal with moderate force. The molded drop-in plug can be forced out with an appropriate tool if the plug is carefully designed and manufactured, using a durable and flexible plastic for the plug, in combination with the correct size for projections 42 and recesses 43. In FIG. 8c, projections 42 have a thinned cross section 61 to act as curved leaf springs to snap in and out of rounded recesses 43.

Whereas these drawings and descriptions shown herein for the purpose of illustrating the invention show one tooth being replaced, the method and apparatus described apply to a multiple tooth replacement site. These and other variations of the present invention may be made which fall within the scope of the appended claims even though such variations were not related above.

The accompanying drawings referred to herein are illustrative of the invention but not restrictive thereto, and, together with the description, serve to explain the principles of the invention.

What is claimed is:

1. A dental restoration having at least one dental implant and at least one dental implant abutment, the at least one abutment having at least one flat shelf;
   a cementable retrievable prosthesis, mating with said at least one abutment, thereby forming a window;
   the prosthesis having at least one flat window ledge in proximity to and parallel to said at least one abutment shelf, forming a gapped space of opposing surfaces for the entrance of a prying instrument,
   the improvement comprising, in combination:
      a conformal plug of resilient durable polymer insertable within said window, said plug having a smooth lingual side, the side being continuous and aligned with said cemented restoration to prevent the ingress of food particles and the concomitant development of bacterial fermentation.

2. A dental restoration having at least one dental implant, and at least one dental implant abutment, the at least one abutment having at least one flat shelf;
   a cementable retrievable prosthesis, mating with said at least one abutment, thereby forming a window;
   the prosthesis having at least one flat window ledge in proximity to and parallel to said at least one abutment shelf, forming a gapped space of opposing surfaces for the entrance of a prying instrument,
   the improvement comprising, in combination:
      a conformal plug of resilient durable polymer insertable within said window, said plug having a smooth lingual side, the side being continuous and aligned with said cemented restoration to prevent the ingress of food particles and the concomitant development of bacterial fermentation;

the conformal plug having molded locking projections matching locking indentations within said window.

3. An apparatus as recited in claim 2 in which said plug is formed by injecting said window with a solidifying compound;

said plug forming in place projections matching said locking indentations within said window; and remaining locked in the hardened state within said window.

4. A method of providing the filling of the apparatus of claim 1, wherein the steps comprise:

injecting said window with a solidifying compound;

forming in place said plug, said plug having said projections;

said projections matching said locking indentations within said window; and said plug remaining locked in the hardened state within said window.

* * * * *